(12) United States Patent
Yang et al.

(10) Patent No.: US 8,366,914 B2
(45) Date of Patent: Feb. 5, 2013

(54) MULTIFUNCTIONAL SCAVENGER FOR HYDROCARBON FLUIDS

(75) Inventors: Jianzhong Yang, Missouri City, TX (US); Tauseef Salma, Sugar Land, TX (US); John A. Schield, Missouri City, TX (US); Jerry J. Weers, Richmond, TX (US); Joseph L. Stark, Richmond, TX (US)

(73) Assignee: Baker Hughes Incorporated, Houston, TX (US)

( * ) Notice: Subject to any disclaimer, the term of this patent is extended or adjusted under 35 U.S.C. 154(b) by 1019 days.

(21) Appl. No.: 12/250,679

(22) Filed: Oct. 14, 2008

(65) Prior Publication Data

US 2009/0095658 A1    Apr. 16, 2009

Related U.S. Application Data

(60) Provisional application No. 60/980,050, filed on Oct. 15, 2007.

(51) Int. Cl.
*C10G 29/20*    (2006.01)
(52) U.S. Cl. ..... 208/236; 208/240; 208/242; 208/254 R; 564/297; 585/833; 585/860
(58) Field of Classification Search .................. 208/236, 208/240, 242, 254 R; 564/297; 585/833, 585/860
See application file for complete search history.

(56) References Cited

U.S. PATENT DOCUMENTS

| | | | |
|---|---|---|---|
| 2,543,953 A | 3/1951 | Backensto | |
| 2,571,666 A | 10/1951 | Bond et al. | |
| 4,927,519 A | 5/1990 | Forester | |
| 5,223,127 A | 6/1993 | Weers et al. | |
| 5,698,696 A | 12/1997 | Marciniak et al. | |
| 6,441,264 B1 * | 8/2002 | Lemaire et al. | 585/833 |

FOREIGN PATENT DOCUMENTS

| | | |
|---|---|---|
| JP | 136239 A | 5/1995 |
| WO | WO2005097300 A1 | 10/2005 |

OTHER PUBLICATIONS

G. H. Meguerian; Organic and Biological Chemistry, "A Kinetic Study of the Oxidation of Mercaptans Catalyzed by Hydroquinone and its Homologs," Journal of the American Chemical Society, Oct. 5, 1955, vol. 77, pp. 5019-5022.

\* cited by examiner

*Primary Examiner* — Prem C Singh
*Assistant Examiner* — Michelle Stein
(74) *Attorney, Agent, or Firm* — Mossman, Kumar & Tyler PC

(57) ABSTRACT

Compounds having the formulae and general formulae:

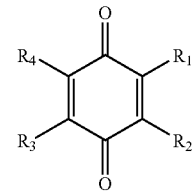

wherein each $R_1$, $R_2$, $R_3$ and $R_4$ are the same or different and may be hydrogen, an alkyl group, an aryl group, a halogen, a nitro group, an alkyl or aryl ester, and an alkyl or aryl ether; compounds having the general formula:

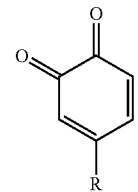

wherein R is an alkyl, aryl or electron withdrawing group;

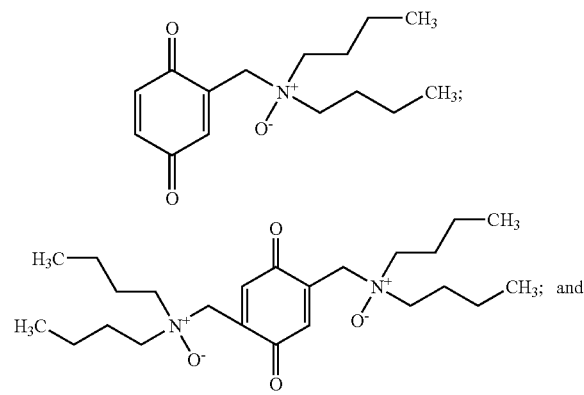

mixtures thereof; can be used as additives for crude oil and hydrocarbons. These compounds may be used to scavenge mercaptans, sulfides, cyanides, and primary or secondary amines; either alone or in combination.

9 Claims, No Drawings

MULTIFUNCTIONAL SCAVENGER FOR HYDROCARBON FLUIDS

CROSS REFERENCE TO RELATED APPLICATIONS

This application claims priority from U.S. Provisional Patent Application Ser. No. 60/980,050 which was filed on Oct. 15, 2007 and is fully incorporated herein by reference.

BACKGROUND OF THE INVENTION

1. Field of the Invention

The present invention relates to scavengers. The present invention particularly relates to scavengers useful for treating crude oil and hydrocarbons.

2. Background of the Art

In the drilling, completions, production, transport, storage, and processing of crude oil and natural gas, including waste water associated with crude oil and gas production, and in the storage of residual fuel oil, mercaptans are often encountered. The presence of mercaptans is objectionable because they often react with other hydrocarbons or fuel system components. Another reason that the mercaptans are objectionable is that they are often highly corrosive. Still another reason that mercaptans are undesirable is that they have highly noxious odors. The odors resulting from mercaptans are detectable by the human nose at comparatively low concentrations and are well known. For example, mercaptans are used to odorize natural gas and used as a repellant by skunks and other animals.

Hydroquinones are known to be useful as mercaptans scavengers. They are used, for example, with a basic solution to catalyze the oxidation of mercaptans to disulfides to regenerates solvents used for mercaptans exactions from crude oil. Even though hydroquinones have been widely used, their use has not been trouble free. For example, the hydroquinones require both a basic solution, such as caustic, and oxygen to be effective.

It would be desirable in the art to scavenge mercaptans using a composition that requires neither oxygen nor a strong base to be effective.

SUMMARY OF THE INVENTION

In one aspect, the invention is an additive useful for treating crude oil and hydrocarbons comprising benzoquinone.

In another aspect, the invention is an additive useful for treating crude oil and hydrocarbons comprising a compound having the general formula:

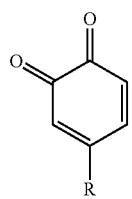

wherein R is an alkyl, aryl, or electron withdrawing group.

In another aspect, the invention is an additive useful for treating crude oil and hydrocarbons comprising compounds having the general formula:

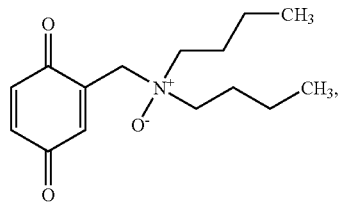

wherein each $R_1$, $R_2$, $R_3$ and $R_4$ are the same or different and may be hydrogen, an alkyl group, an aryl group, a halogen, a nitro group, an alkyl or aryl ester, and an alkyl or aryl ether.

In still another aspect, the invention is a an additive useful for treating crude oil and hydrocarbons comprising at least one compound select from the group consisting of:

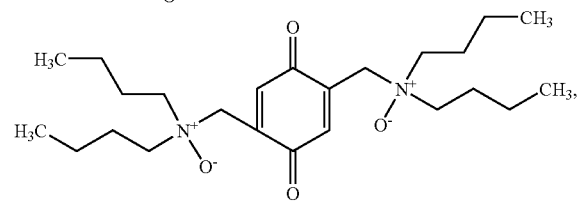

and mixtures thereof.

In still another embodiment, the invention is a method for treating a crude oil or a hydrocarbon comprising admixing crude oil or a hydrocarbon with an additive having at least one compound selected from the group consisting of compounds having the general formula:

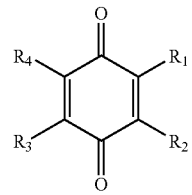

wherein each $R_1$, $R_2$, $R_3$ and $R_4$ are the same or different and may be hydrogen, an alkyl group, an aryl group, a halogen, a nitro group, an alkyl or aryl ester, and an alkyl or aryl ether; compounds having the general formula:

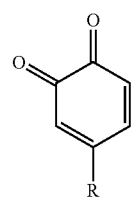

wherein R is an alkyl or aryl group;

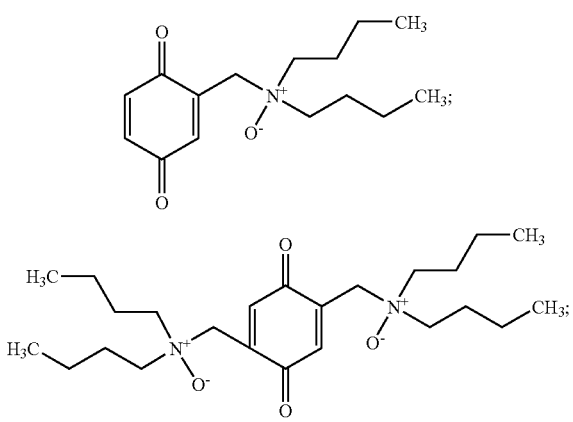

and mixtures thereof.

DESCRIPTION OF THE PREFERRED EMBODIMENTS

In one embodiment, the present invention is an additive useful for treating crude oil and hydrocarbons. For the purposes of the present invention, crude oil is the fluid produced from an oil and gas well after most of the water and gases have been separated. The crude oil and hydrocarbons which may be treated using the method of the invention may have from undetectable levels of water to as much as 95 percent water. Often crude oil will have as much as about 15 weight percent water. In one embodiment, the crude oil and hydrocarbons may have from about 1 percent to about 10 percent water.

The hydrocarbons which may be treated using the method of the invention include any that are substantially hydrophobic. For example, fuel oils may be treated with the method of the invention. Organic chemicals and intermediates may also be treated with the method of the invention.

The additives of the invention may be used to "scavenge" mercaptans. The term "scavenge" means to either remove or change a compound such that it is less undesirable. For example, in the prior art, mercaptans were described as being scavenged by being oxidized to disulfides. The disulfides were less corrosive than the mercaptans from which they were derived and thus less undesirable.

In addition to mercaptans, other classes of compounds that may be undesirable in either crude oil or hydrocarbons may be "scavenged" using the method of the invention. For example, sulfides and cyanides may be scavenged using the method of the invention. Sulfides and cyanides may be undesirable because they can render corrosion issues in downstream units even at very low ppm level. Also, they can generate highly toxic species that pose an acute health hazard. Primary and secondary amines, which may cause serious overhead corrosion and quality issue to petrochemical products, may also be scavenged using the method of the invention.

The additives useful with the method of the invention, may, in one embodiment, be prepared using benzoquinone. In another embodiment, the method of the invention may be practiced with additives including a compound having the general formula:

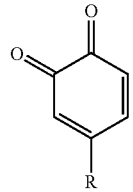

wherein R is an alkyl or aryl group. Exemplary compounds include those where the R group is hydrogen, butyl, octyl, nonyl, or with electron withdrawing groups. For example, in one embodiment of the invention, the R group is an alkyl group having from 1 to 20 carbons. In another embodiment, the R group is an alkyl group having from 4 to 12 carbons. For the purposes of this application, an electron withdrawing group is one that has a deactivating effect upon electrophilic aromatic substitution and is selected from the group consisting of —C(=O)R, —COOR, —N$^+$R$_3$, —CN, —NO$_2$ etc (where R=H or alkyl or aryl group).

In still another embodiment, the method of the invention may be practiced using additives including compounds having the general formula:

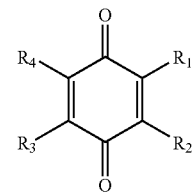

wherein each $R_1$, $R_2$, $R_3$ and $R_4$ are the same or different and may be hydrogen, an alkyl group, an aryl group, a halogen, a nitro group, an alkyl or aryl ester, and an alkyl or aryl ether. For example, in one embodiment, $R_2$, $R_3$ and $R_4$ are hydrogen and $R_1$ is an alkyl group having from 1 to 12 carbons.

In another embodiment, the method of the invention may be practiced with additives including:

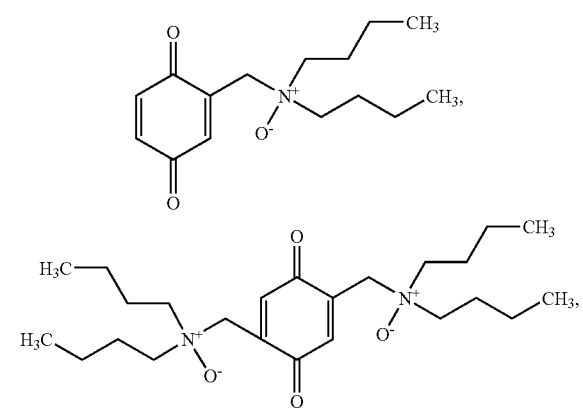

and mixtures thereof.

The additives of the present invention may be used in any way known to be useful to those of ordinary skill in the art of treating crude oil and hydrocarbons. For example, the additives may be used in the presence of a strong base such as sodium hydroxide and molecular oxygen. In another example of an embodiment of the invention, the additives may be used in the absence of one or both of sodium hydroxide and molecular oxygen.

Similarly, the additives may be admixed in any way known to be useful. For example, they may be added to a feed line or directly into a vessel. In one embodiment, the feed line may include a static or powered mixer. In another embodiment, the additive may be admixed by atomization into a vapor stream. In another embodiment, the vessel may include mixer or a recycle that effects mixing. In still another embodiment, the additives may be added to a pipeline and admixed by turbulence. Similarly, the additives may be added to a tank truck and mixed by the movement of the crude oil or hydrocarbon being treated with the truck.

The additives of the invention may be added in near stochiometric amounts when the concentration of targeted contaminants and interfering compounds are known. When such concentrations are not known, then the correct dosage may be determined using jar tests or any other method well known to those of ordinary skill in the art of producing and refining crude oil and producing hydrocarbons. The additives may be used at temperatures ranging from about 0 to about 800° F.

The additives may include other compounds in addition to the components already disclosed. For example, the scavengers may also include: aromatic solvents, base, or organic oxidizers. The additives may also be prepared with any aprotic solvent such as, but not limited to dichloromethane, chloroform, tetrahydrofuran, N-methyl pyrrolidone, dimethyl sulfoxide (DMSO), dimethyl formamide (DMF), diglyme and the like.

EXAMPLES

The following examples are provided to illustrate the invention. The examples are not intended to limit the scope of the invention and they should not be so interpreted. Amounts are in volume parts or volume percentages unless otherwise indicated.

Example 1

A sample of toluene and hexane having a known amount mercaptans recorded below in Table 1 as ppm methyl mercaptans is treated with an additive of the invention wherein the additive is prepared with 20 weight percent benzoquinone in DMF. The sample is dosed with the benzoquinone solution and then shaken at 50° C. for the time indicated and is then tested according to ASTM-D3227. The results are shown below in Table 1.

Example 2

Example 1 is repeated substantially identically except that naphtha is used instead of toluene and hexane mixture. The conditions and results are shown below in Table 2.

Example 3

Example 1 is repeated substantially identically except that crude oil is used instead of toluene and hexane mixture. The conditions and results are shown below in Table 3.

TABLE 1

| Toluene | | |
|---|---|---|
| Scavenger Dose (volume ppm Benzoquinone solution) | PPM $C_4SH$ | Treatment Time (hours) |
| 0 | 131 | — |
| 500 | 122 | 1 |
| 1000 | 62 | 1 |
| 2000 | 0 | 1 |
| 3000 | 0 | 1 |

TABLE 2

| Naphtha | | |
|---|---|---|
| Scavenger Dose (weight ppm Benzoquinone solution) | PPM SH | Treatment Time (hours) |
| 0 | 907 | — |
| 4000 | 551 | 1 |
| 4000 | 453 | 24 |

TABLE 3

| Crude Oil | | |
|---|---|---|
| Scavenger Dose (volume ppm Benzoquinone solution) | PPM SH | Treatment Time (hours) |
| 0 | 364 | 24 |
| 500 | 351 | 24 |
| 1000 | 297 | 24 |
| 2000 | 219 | 24 |
| 3000 | 169 | 24 |

Brief Discussion of the Examples

The Examples illustrate that benzoquinone is effective at scavenging mercaptans.

Example 4

A stock solution of 1000 ppm benzylamine was prepared in aromatic solvent. The amine stock solution was then treated at room temperature with 20 weight percent benzoquinone in DMF. The amine content was analyzed with FID-GC. The results are shown below in Table 4.

TABLE 4

| Scavenger Dose (ppm Benzoquinone) | PPM Benzylamine |
|---|---|
| 0 | 990 |
| 200 | 920 |
| 400 | 900 |
| 800 | 695 |
| 1200 | 0 |

What is claimed is:

1. A method for treating a crude oil or a hydrocarbon comprising admixing crude oil or a hydrocarbon with an additive comprising at least one compound selected from the group consisting of:

compounds having the general formula:

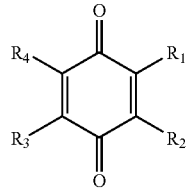

wherein each $R_1$, $R_2$, $R_3$ and $R_4$ are the same or different and selected from the group consisting of hydrogen, an alkyl group, an aryl group, a halogen, a nitro group, an alkyl ester, an aryl ester, an alkyl ether, and an aryl ether;

compounds having the general formula:

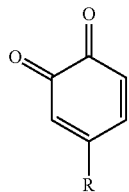

wherein R is an alkyl or aryl group;

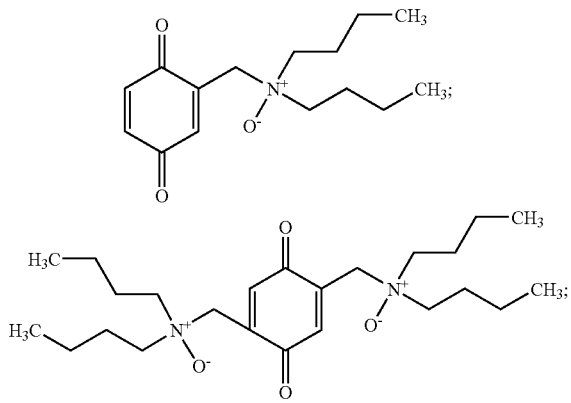

and mixtures thereof;

wherein the additive functions to scavenge mercaptans, sulfide, cyanides, primary amines and secondary amines; and the method is practiced in the absence of a strong base.

2. The method of claim 1 wherein the additive has the general formula:

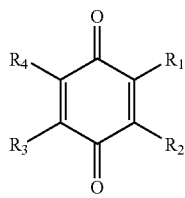

and $R_1$, $R_2$, $R_3$ and $R_4$ are each hydrogen.

3. The method of claim 1 wherein the additive has the general formula:

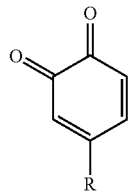

and R is an alkyl, aryl, or electron withdrawing group.

4. The method of claim 3 wherein R is selected from the group consisting of hydrogen, butyl, octyl, and nonyl groups.

5. The method of claim 1 wherein the method is practiced in the presence of water.

6. The method of claim 1 wherein the water is present at a total concentration for from about 1 to about 15 percent by weight.

7. The method of claim 1 wherein the hydrocarbon is a fuel oil.

8. The method of claim 1 wherein the hydrocarbon is an organic chemical.

9. The method of claim 1 wherein the additive functions to scavenge mercaptans.

* * * * *